US00PP22457P2

(12) United States Plant Patent
Hansen

(10) Patent No.: US PP22,457 P2
(45) Date of Patent: Jan. 10, 2012

(54) *SEDUM* PLANT NAMED 'RAZZLEBERRY'

(50) Latin Name: ***Sedum* hybrid**
Varietal Denomination: Razzleberry

(76) Inventor: Christopher M. Hansen, Holland, MI (US)

( * ) Notice: Subject to any disclaimer, the term of this patent is extended or adjusted under 35 U.S.C. 154(b) by 0 days.

(21) Appl. No.: 13/199,312

(22) Filed: Aug. 25, 2011

(51) Int. Cl.
*A01H 5/00* (2006.01)

(52) U.S. Cl. ..... Plt./479

(58) Field of Classification Search ..... Plt./479
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of *Sedum* plant named 'Razzleberry' characterized by its very compact plant habit with stems that do not flop, its size of about 22 cm (9 inches) in height and 46 cm (18 inches) in spread, its very large inflorescences up to 22 cm (9 inches) in diameter, its flowers that are dark raspberry red in color, its foliage that emerges gray-blue in spring and turns to dark purple-black in mid summer, its very early blooming season, and its resistance to *Sedum* foliage blight.

2 Drawing Sheets

Botanical classification: *Sedum* hybrid.
Variety denomination: 'Razzleberry'.

BACKGROUND OF THE INVENTION

The present invention relates to a new and distinct cultivar of *Sedum* plant of hybrid origin known as *Sedum* 'Razzleberry' and will be referred to hereinafter by its cultivar name, 'Razzleberry'. The new cultivar of *Sedum* is a hardy herbaceous perennial grown for use as a landscape and container plant with particular use as a groundcover.

'Razzleberry' arose from an ongoing breeding program conducted by the Inventor in Hudsonville, Mich. The goal of the breeding program is to produce new groundcover type cultivars of *Sedum* with compact, mounding, plant habits without the tendency to flop combined with abundant, large, and brightly colored flowerheads.

The inventor made a cross in September 2009 between an unnamed plant from the Inventor's breeding program as the female parent, and Xenox (U.S. Plant Pat. No. 16,888) as the male parent. 'Razzleberry' was selected as a single unique plant in August 2010 amongst the seedlings that resulted from the above cross.

Asexual reproduction of the new cultivar was first accomplished by tip cuttings in September of 2010 in Hudsonville, Mich. Propagation by cuttings has determined the characteristics are stable and reproduced true to type in successive generations.

SUMMARY OF THE INVENTION

The following traits have been repeatedly observed and are determined to be the characteristics of the new cultivar. These attributes in combination distinguish 'Razzleberry' as a unique cultivar of *Sedum*.

1. 'Razzleberry' exhibits a very compact plant habit with stems that do not flop.
2. 'Razzleberry' reaches about 22 cm (9 inches) in height and 46 cm (18 inches) in spread.
3. 'Razzleberry' exhibits very large inflorescences up to 22 cm (9 inches) in diameter.

4. 'Razzleberry' exhibits flowers that are dark raspberry red in color.
5. 'Razzleberry' exhibits foliage that emerges gray-blue in spring and turns to dark purple-black in mid summer.
6. 'Razzleberry' blooms very early in the season.
7. 'Razzleberry' has been observed to be highly resistant to *Sedum* foliage blight.

'Razzleberry' can be compared to its parent plants. The female parent differs from 'Razzleberry' in having a plant size that is half the size (reaches 10 cm in height), inflorescences that are much smaller in size (5 cm in diameter), smaller leaves, and gray-green foliage that does not change to purple-black in summer. The male parent, Xenox differs from 'Razzleberry' in being larger in size and less compact, in having flowers that are light pink in color, and in having larger leaves. 'Razzleberry' can also be most closely compared to the cultivars 'Sunset Cloud' (not patented) and 'Rosy Glow' (not patented). 'Sunset Cloud' and 'Rosy Glow' differ from 'Razzleberry' in being taller in height, in having an open and floppy plant habit with age, in having smaller inflorescences with fewer flowers per inflorescence, and in having smaller, thinner leaves with longer internode lengths.

BRIEF DESCRIPTION OF THE DRAWINGS

The accompanying colored photographs illustrate the overall appearance and distinct characteristics of the new *Sedum*. The photographs were taken of 2 year-old plants of 'Razzleberry' as grown in the ground in full sun in Hudsonville, Mich.

The photograph in FIG. 1 provides a view of the plant habit of several plants of 'Razzleberry'.

Figure 1:
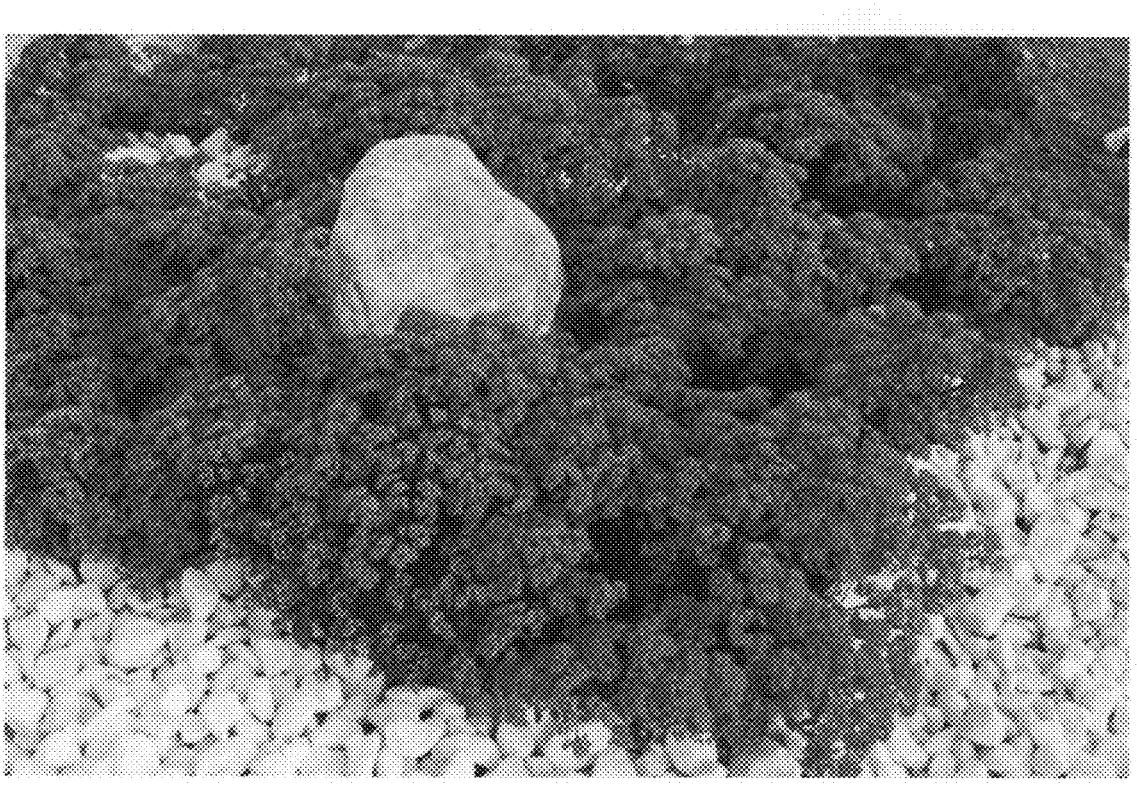
Figure 2:
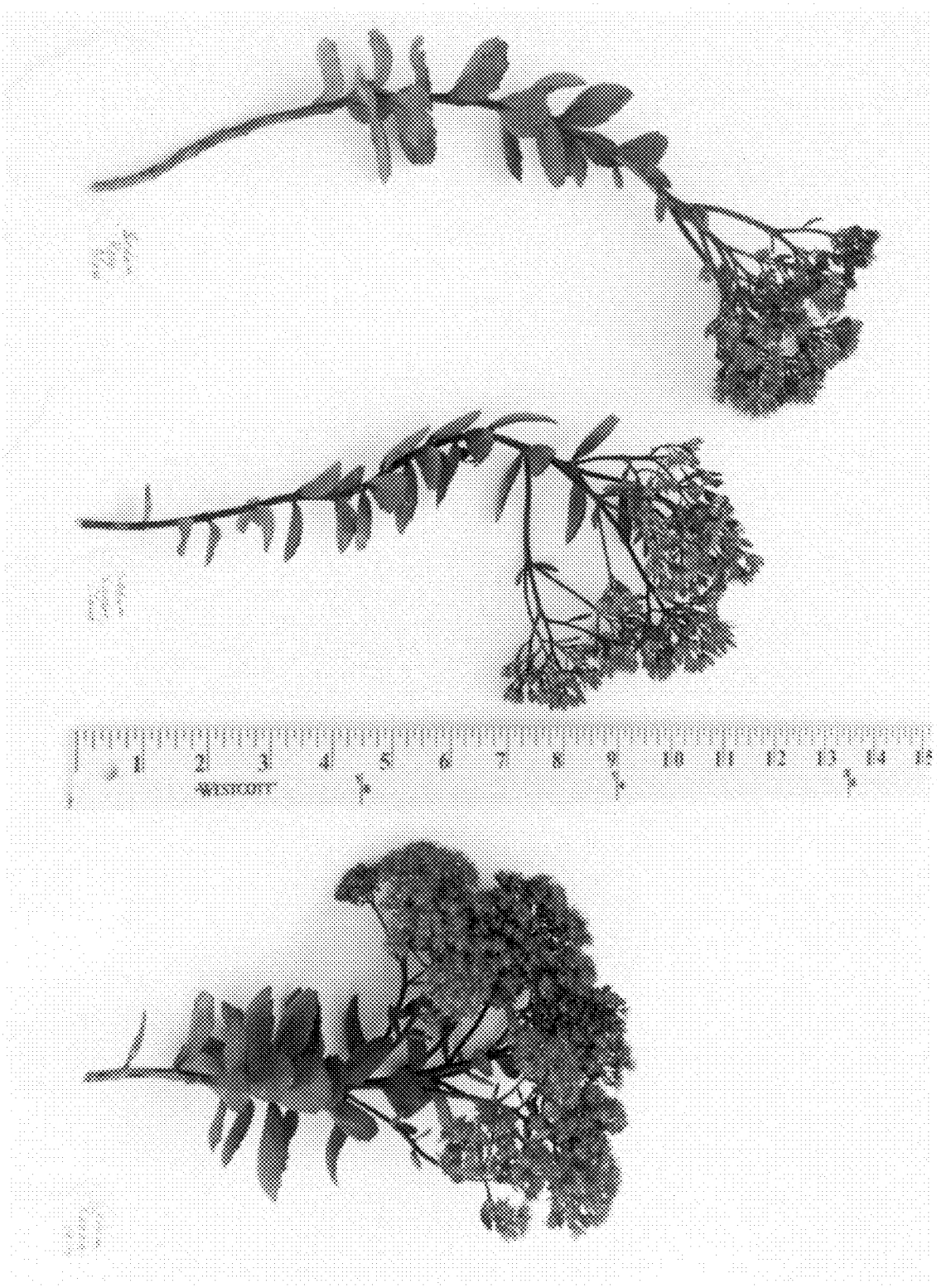

The photograph in FIG. 2 provides a comparison between blooming stems of 'Razzleberry' (bottom), 'Sunset Cloud' (center) and 'Rosy Glow' (top).

The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 2 year-old plants of 'Razzleberry' as grown in a garden in full sun in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Very early blooming, about 5 weeks in mid summer in Michigan.

*Plant type.*—Herbaceous perennial.

*Plant habit.*—Compact, tightly mounded, with flower stems that are held upright and do not flop.

*Height and spread.*—Reaches about 22 cm in height when in bloom and about 46 cm in spread.

*Hardiness.*—At least in U.S.D.A. Zones 4 to 9.

*Diseases.*—Observed to be highly resistant to *Sedum* foliage blight.

*Root description.*—Fibrous.

*Propagation.*—Tip stem cuttings preferred.

*Growth rate.*—Vigorous.

Stem description:

*Stem shape.*—Round.

*Stem size.*—Up to 22 cm in length (including terminal peduncle) and an average of 4 mm in width.

*Internode length.*—Average of 5 cm.

*Stem color.*—59A with very fine striations of 161C (not conspicuous).

*Stem surface.*—Glabrous.

*Branching habit.*—Basal or near-basal branching.

Foliage description:

*Leaf shape.*—Elliptic.

*Leaf division.*—Simple.

*Leaf arrangement.*—Whorled (sometime opposite).

*Leaf base.*—Cuneate.

*Leaf apex.*—Broadly acute.

*Leaf venation.*—Not conspicuous, color matched leaf color on both surfaces.

*Leaf margins.*—Crenate to serrated on upper half of lower stems leaves, mostly entire near apex and on peduncles.

*Leaf attachment.*—Sessile.

*Leaf presence and orientation.*—An average of 45° angle to stem.

*Leaf texture.*—Thick, succulent.

*Leaf surface.*—Glandular and slightly glaucous on both surfaces.

*Leaf color.*—Spring and early summer upper surface, 137B and suffused with N77A and base suffused with 59B, spring and early summer lower surface, 189B with small flecks of N77A, new leaves late summer, upper and lower surface; a blend of 189A and 189B, mature leaves late summer upper surface; 137A and heavily suffused with N187A, mature leaves late summer lower surface; N137A with glaucous coating of 189A.

*Leaf size.*—Up to 3.5 cm in length and 2 cm in width.

Flower description:

*Inflorescence type.*—Dense, slightly rounded cymes with an average of 8 terminal forked branches at terminus and upper lateral nodes.

*Inflorescence size.*—Up to 22 cm in width and 20 cm in depth.

*Lastingness of inflorescence.*—At least one month.

*Flower type.*—Perfect, spreading, 5-starred.

*Flower number.*—An average of 80 flowers per branched cyme, about 800 flowers per stem.

*Flower fragrance.*—None.

*Flower buds.*—Conical in shape, about 5 mm length and 3 mm in diameter, ribbed surface, color; 189C with stripes of 58A.

*Flower size.*—About 5 cm in depth and 8 cm in diameter.

*Peduncles.*—Slightly oval in shape, primary range from 1.5 to 5 cm in length, an average of 2.5 mm in width, secondary average 1.3 cm in length and 1.5 mm in width, 59A in color, glabrous surface, peduncle leaves; an average of 2 per individual cyme, elliptic in shape, an average of 1 cm in length and 5 mm in width, 191B in color and heavily suffused with 59A, glaucous surface.

*Pedicels.*—Slightly oval in shape, range from 1.5 to 5 cm in length, an average of 2.5 mm in width, 191B in color and lightly suffused with 59A, glabrous surface.

*Sepals.*—5, 1.5 cm in length and 0.7 cm in width, lanceolate in shape, 191B in color with small spots of 59A on both surfaces, entire margin, narrowly acute apex, fused base, glaucous on both surfaces.

*Petals.*—5, spreading, about 5 mm in length and 1.5 mm in width, lanceolate in shape, truncate base, acute apex, entire margin, color of inner and outer surfaces when opening and mature; a blend of NN155A and heavy shading, spots and stripes of 58A, glabrous surfaces on both surfaces.

Reproductive organs:

*Pistils.*—5, showy, held erect, about 3.5 mm in length, stigma; 1 mm in width and 58A in color, style; 2.5 mm in length, 1.2 mm in width, lanceolate in shape and color NN155A with heavy shading of 58A, ovary; small, single celled and translucent in color.

*Stamens.*—10, about 4 mm in length, filament; very fine and 58A in color, anther; acorn-shaped, about 0.5 mm in length and width and 83A in color, pollen is moderate in quantity and 11D in color.

*Fruit and seed.*—Seed production was not observed.

It is claimed:

1. A new and distinct variety of *Sedum* plant named 'Razzleberry' as described and illustrated herein.

* * * * *

UNITED STATES PATENT AND TRADEMARK OFFICE

CERTIFICATE OF CORRECTION

PATENT NO. : PP22,457 P2
APPLICATION NO. : 13/199312
DATED : January 10, 2012
INVENTOR(S) : Christopher M. Hansen It is certified that error appears in the above-identified patent and that said Letters Patent is hereby corrected as shown below:

Title Page, Item (54) In the Title:
Delete "'Razzleberry'" and insert --'Dazzleberry'--

Title Page, Item (57) In the Abstract:
Delete "'Razzleberry'" and insert --'Dazzleberry'--

Please change the following in the appropriate location on the specification:

Column 1, line 2, In the Variety Denomination:
Delete "'Razzleberry'" and insert --'Dazzleberry'--

Column 1, lines 7-8, 9, 12, 21, In the Background of the Invention:
Delete "'Razzleberry'" and insert --'Dazzleberry'--

Column 1, lines 34, 36, 38, 40; Column 2, lines 1, 3, 5, 6, 8, 9, 14, 16, 19, In the Summary of the Invention:
Delete "'Razzleberry'" and insert --'Dazzleberry'--

Column 2, lines 27-28, 31, 33, In the Description of the Drawings:
Delete "'Razzleberry'" and insert --'Dazzleberry'--

Column 2, line 41, In the Detailed Botanical Description:
Delete "'Razzleberry'" and insert --'Dazzleberry'--

Column 4, line 53, In the Claim:
Delete "'Razzleberry'" and insert --'Dazzleberry'--

Signed and Sealed this
Fifteenth Day of May, 2012

David J. Kappos

David J. Kappos
*Director of the United States Patent and Trademark Office*